United States Patent [19]
Kovac et al.

[11] Patent Number: 5,269,792
[45] Date of Patent: Dec. 14, 1993

[54] SURGICAL CLIP

[75] Inventors: Tim Kovac, Los Gatos; Terrance Kloeckl, Palo Alto; Jay Daulton, San Jose, all of Calif.; Peter F. Costa, Winthrop; William A. Holmes, Marblehead, both of Mass.; Richard J. Saunders, Redwood City, Calif.

[73] Assignee: Origin Medsystems, Inc., Menlo Park, Calif.

[21] Appl. No.: 957,970

[22] Filed: Oct. 7, 1992

Related U.S. Application Data

[63] Continuation-in-part of Ser. No. 908,709, Jul. 2, 1992, abandoned, which is a continuation-in-part of Ser. No. 888,723, May 26, 1992, Pat. No. 5,192,288.

[51] Int. Cl.⁵ .............................................. A61B 17/00
[52] U.S. Cl. .................................... 606/158; 606/157
[58] Field of Search ............... 606/151, 157, 158, 143; 227/901, 902

[56] References Cited

U.S. PATENT DOCUMENTS

| | | | |
|---|---|---|---|
| 3,363,628 | 1/1968 | Wood | 128/325 |
| 3,439,523 | 4/1969 | Wood | 72/410 |
| 3,463,156 | 8/1969 | McDermott | 128/325 |
| 3,665,924 | 5/1972 | Noiles et al. | 128/305 |
| 3,675,688 | 7/1972 | Bryan et al. | 140/93 D |
| 3,683,927 | 8/1972 | Noiles | 128/334 R |
| 4,086,926 | 5/1978 | Green et al. | 128/334 R |
| 4,146,130 | 3/1979 | Samuels et al. | 206/340 |
| 4,509,518 | 4/1985 | McGarry et al. | 128/325 |
| 4,616,650 | 10/1986 | Green et al. | 128/325 |
| 4,799,481 | 1/1989 | Transue et al. | 128/325 |
| 4,976,722 | 12/1990 | Failla | 606/157 |

Primary Examiner—Stephen C. Pellegrino
Assistant Examiner—Gary Jackson
Attorney, Agent, or Firm—Townsend and Townsend Khourie and Crew

[57] ABSTRACT

The invention provides a surgical clip for use in conjunction with a clip applier. The clip may be closed in a curved shape, has improved gripping capabilities, and maximizes the gripping surface relative to clip size. The clip preferably includes a longitudinal channel through the gripping surfaces of the clip legs, the channel having at least one sidewall inclined to form an undercut, such that the channel is wider at its floor than at its opening in the gripping surface. The clip further may have one leg longer than the other such that the clip may be closed in a curved shape with the legs parallel and the tips of the legs substantially even. The clip may also have one or more inverse arcuate portions on at least one of its legs to improve the tightness of clip closure.

64 Claims, 14 Drawing Sheets

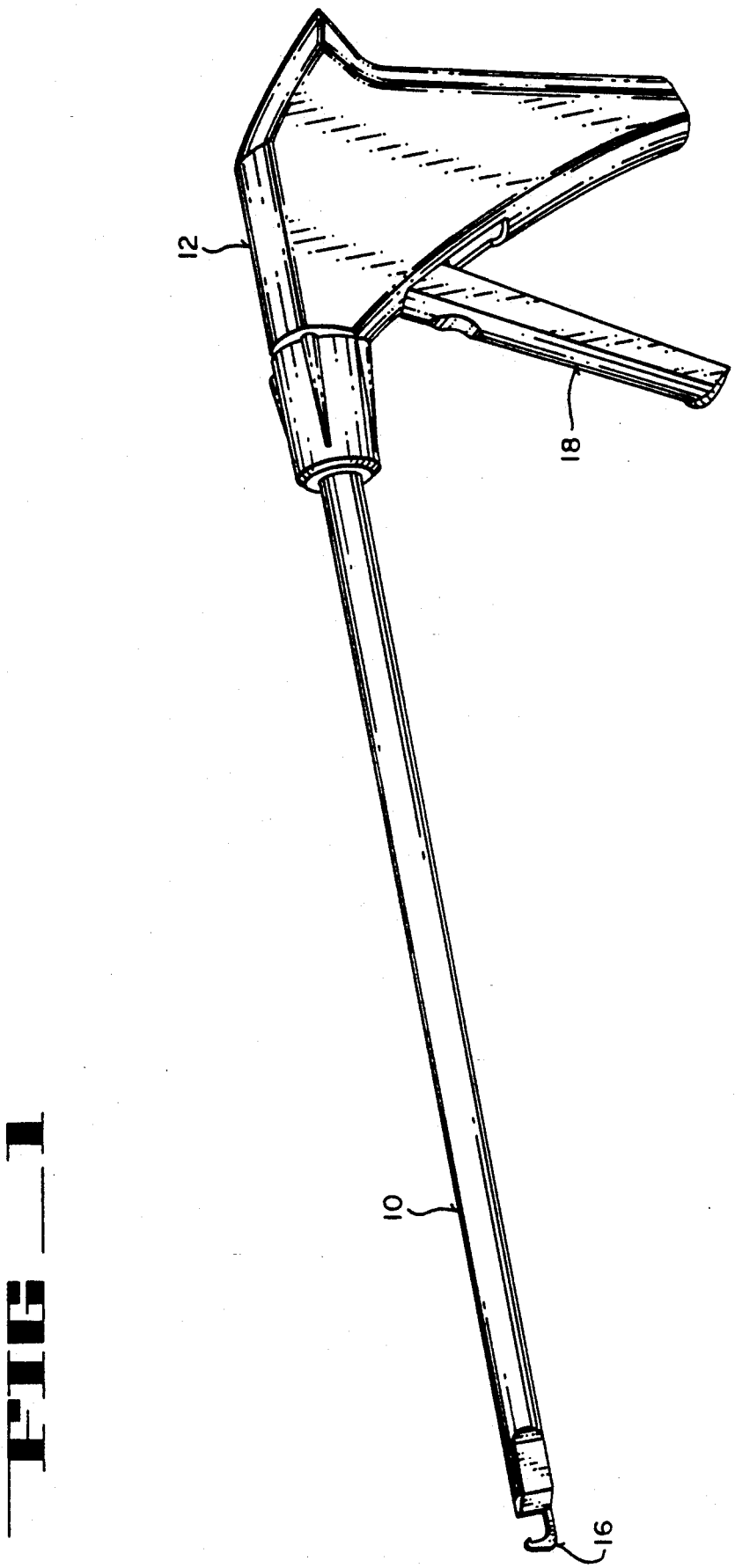

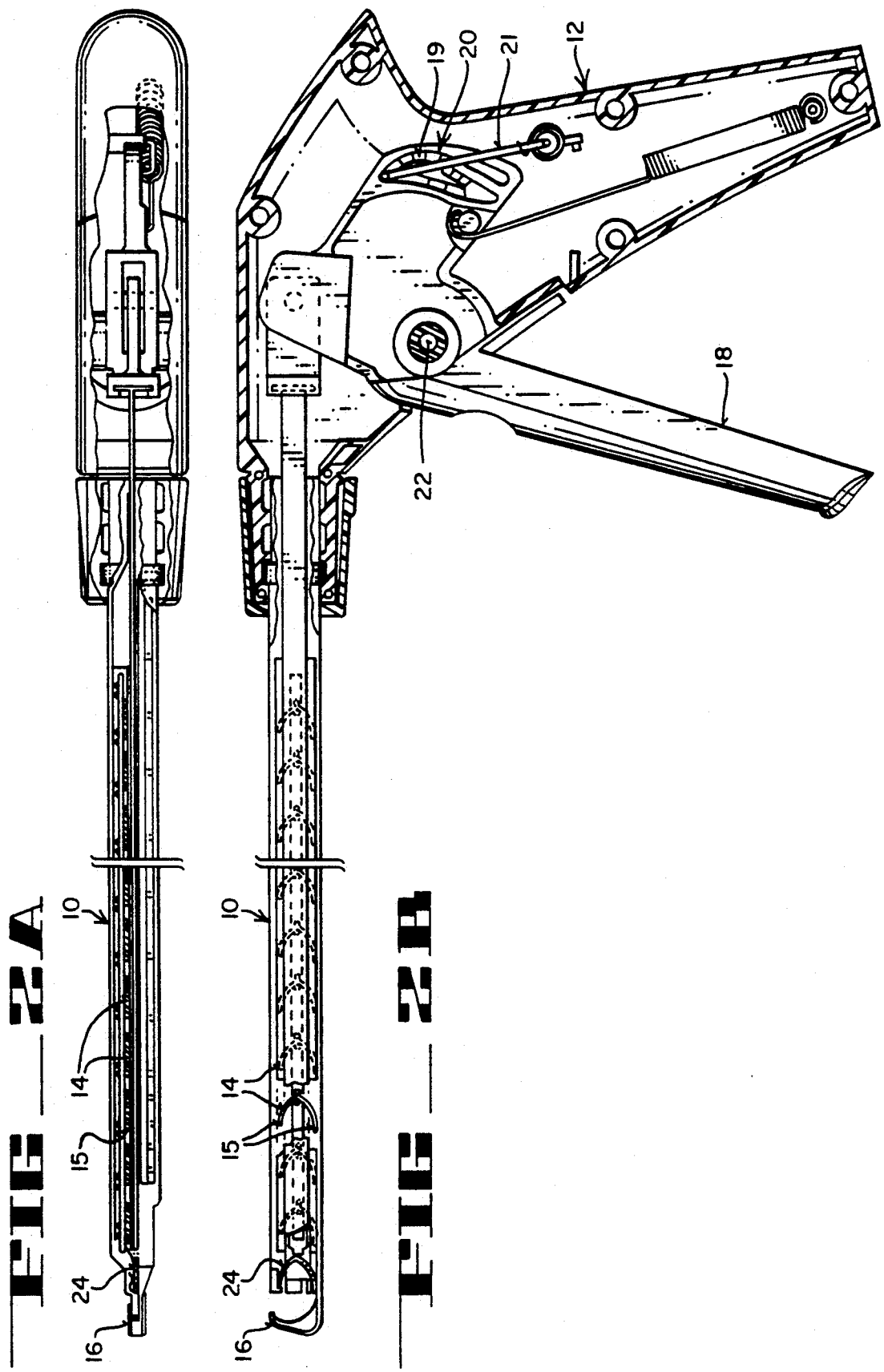

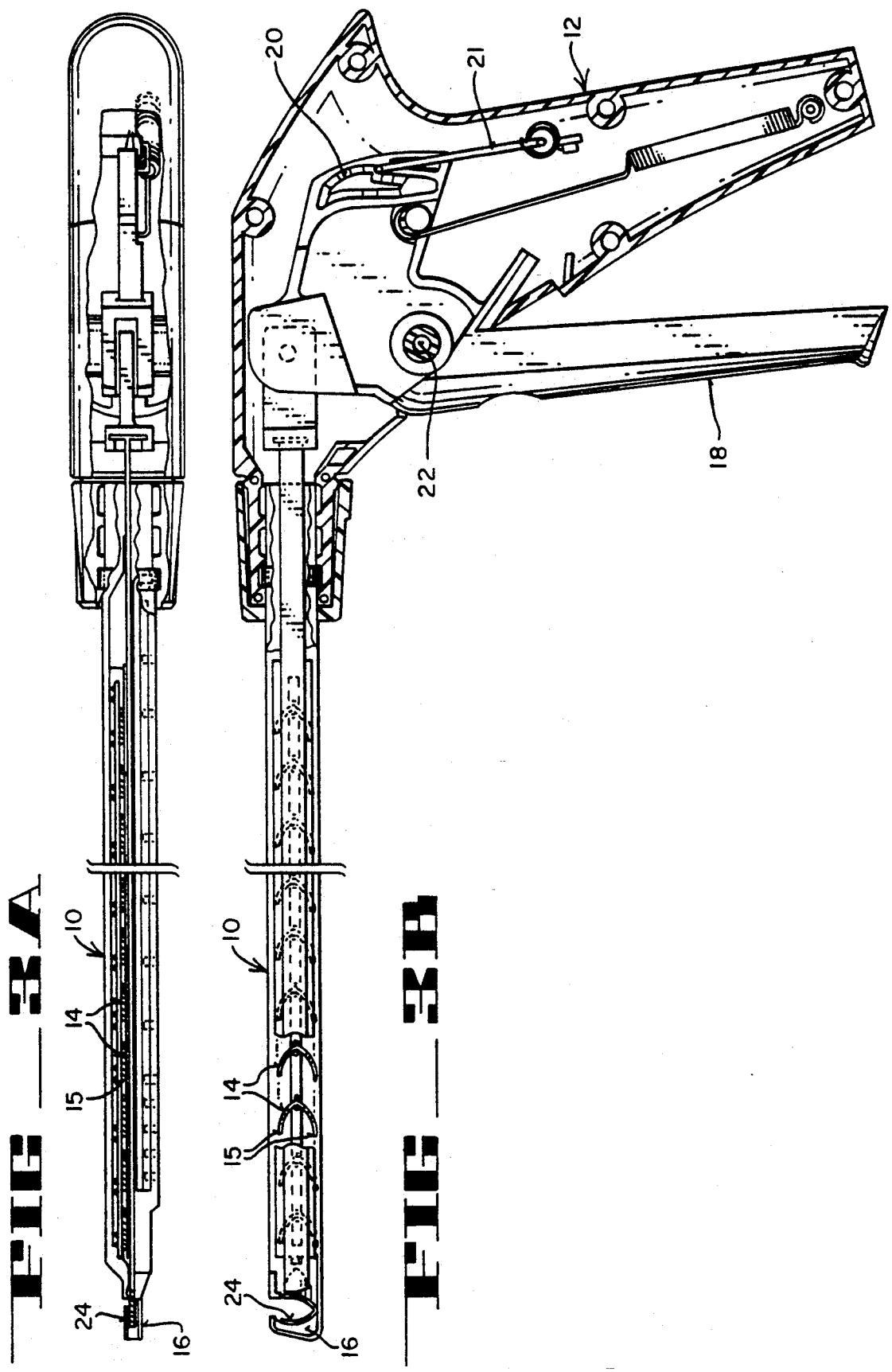

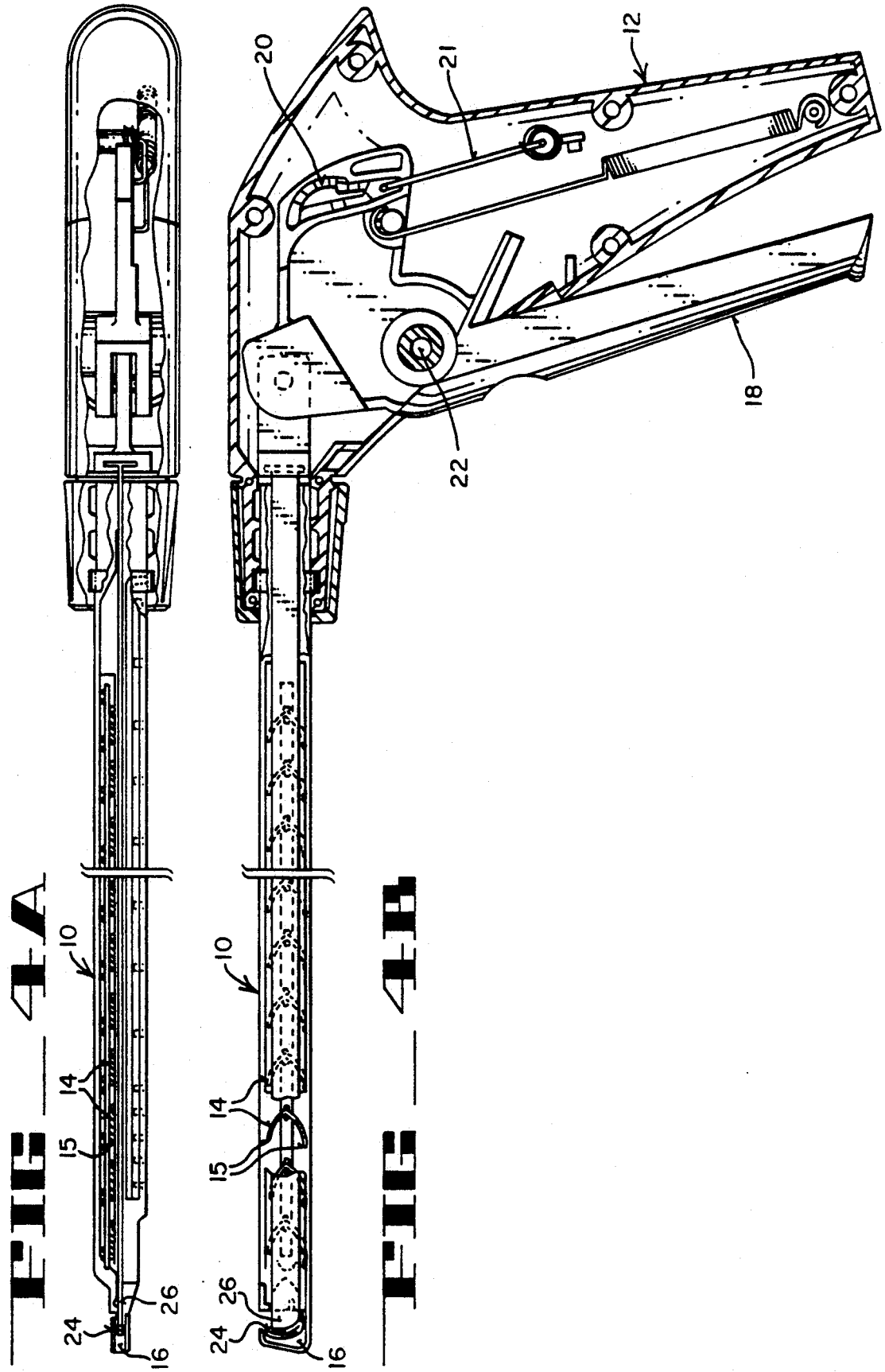

FIG_5A
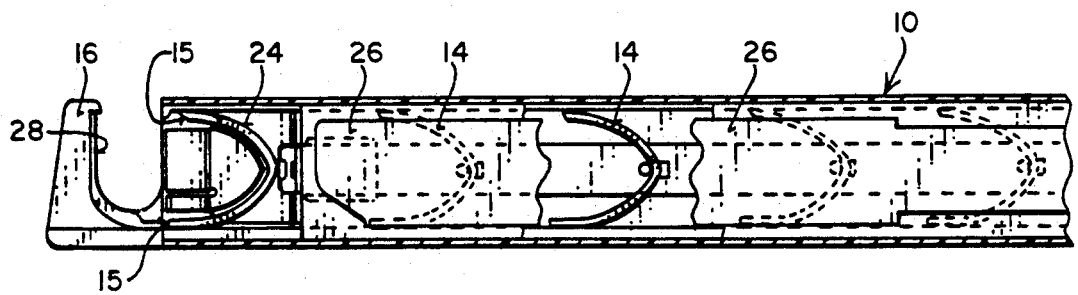
FIG_5B
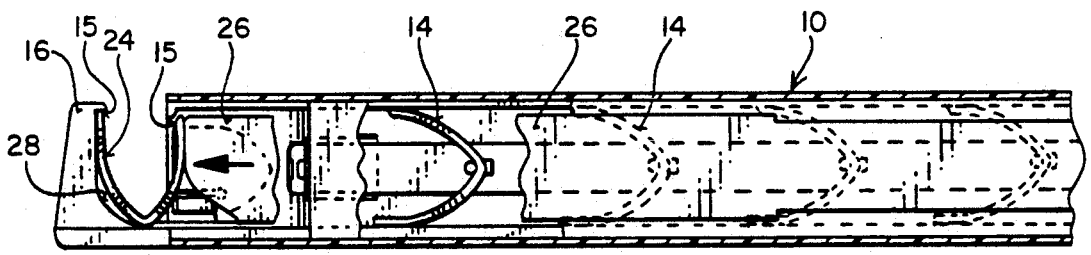
FIG_5C
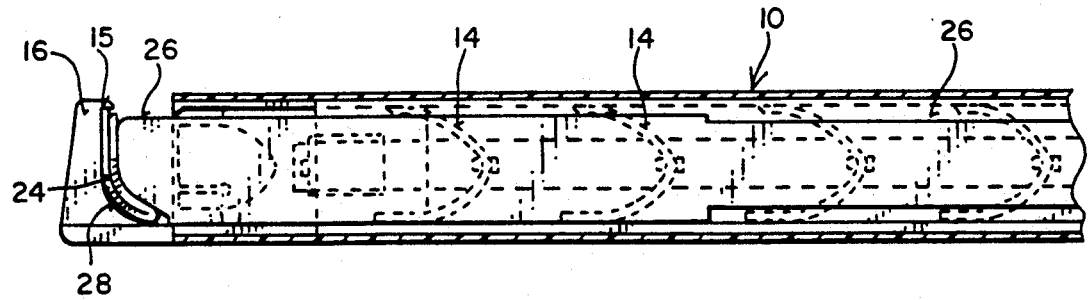

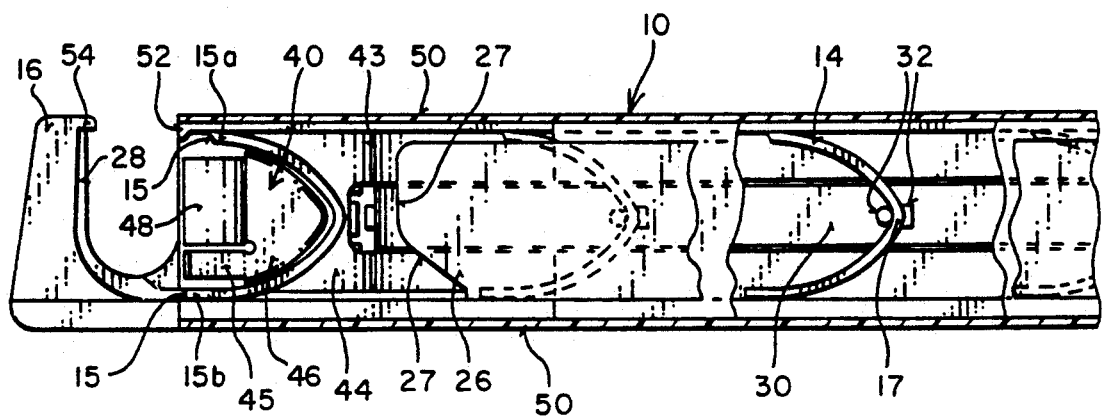
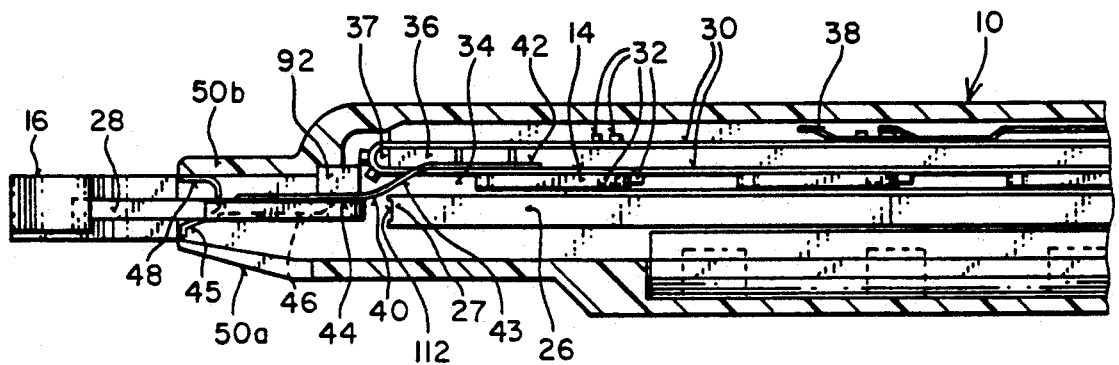
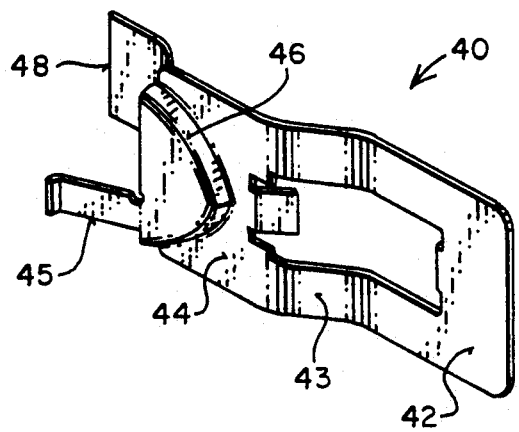

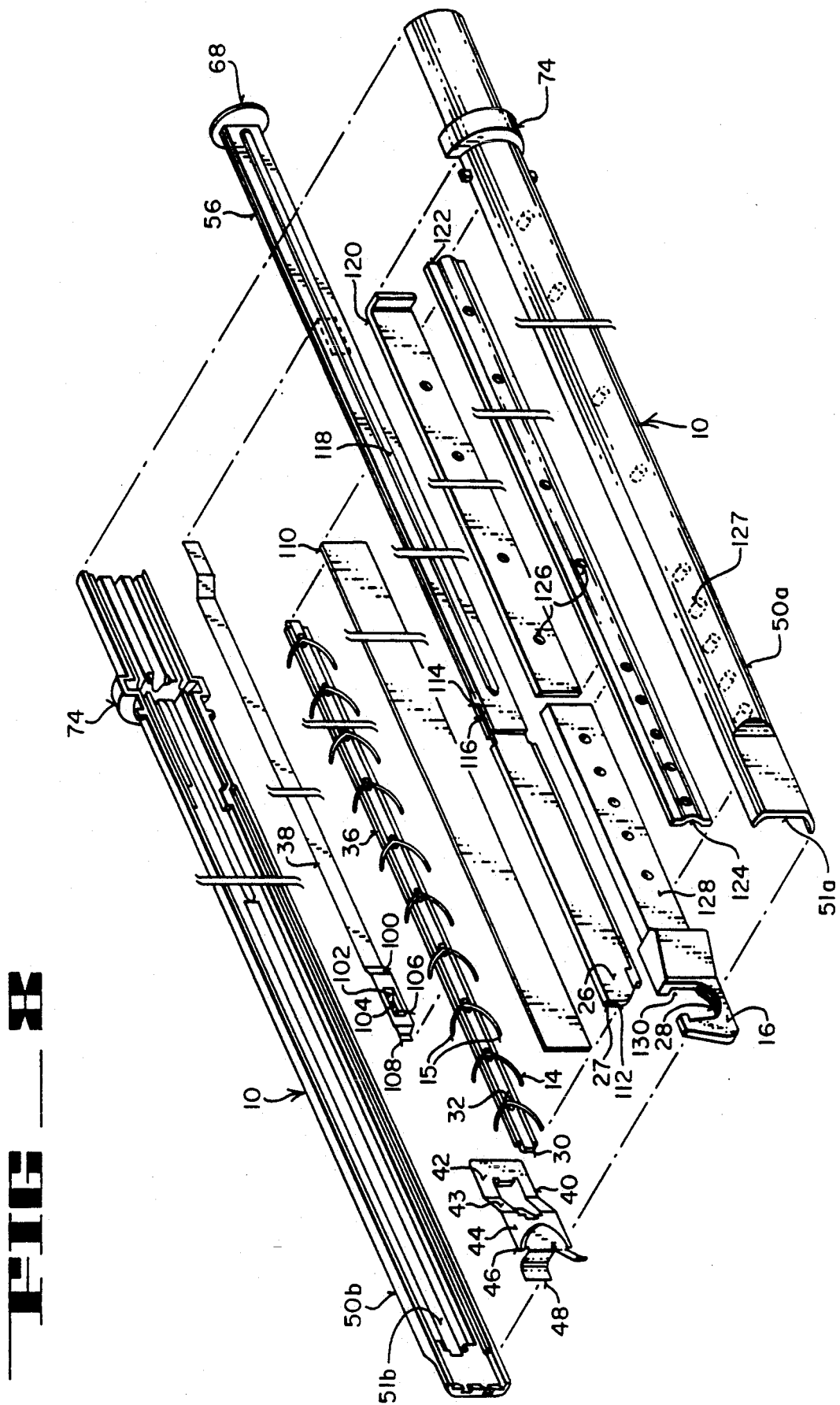

FIG_9A
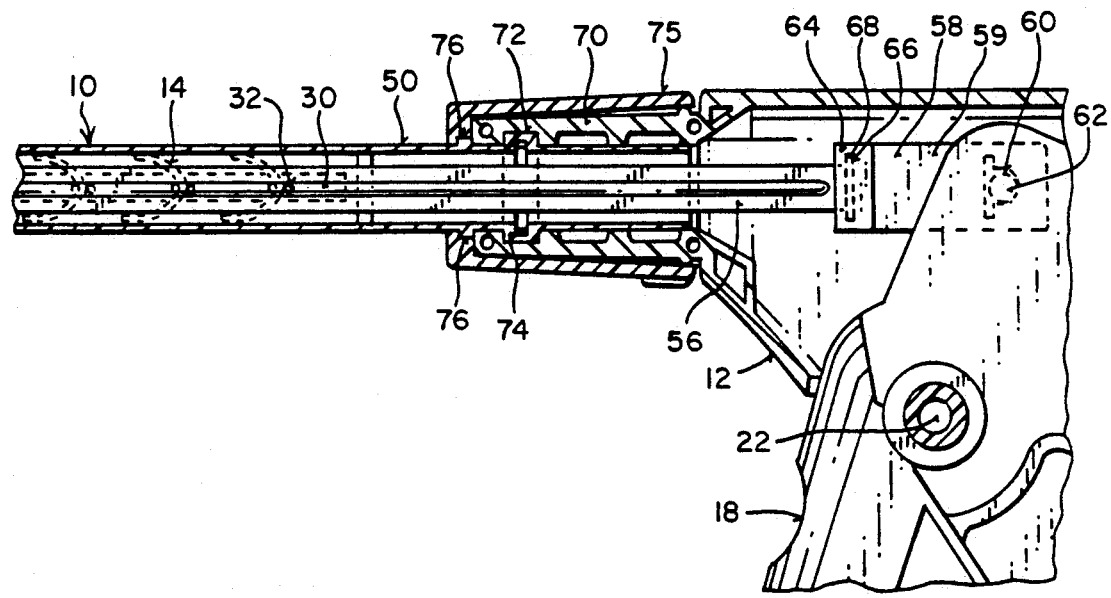
FIG_9B
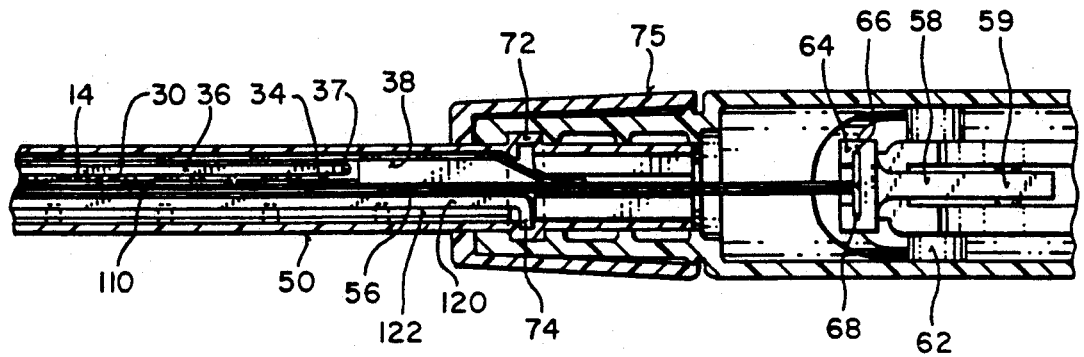

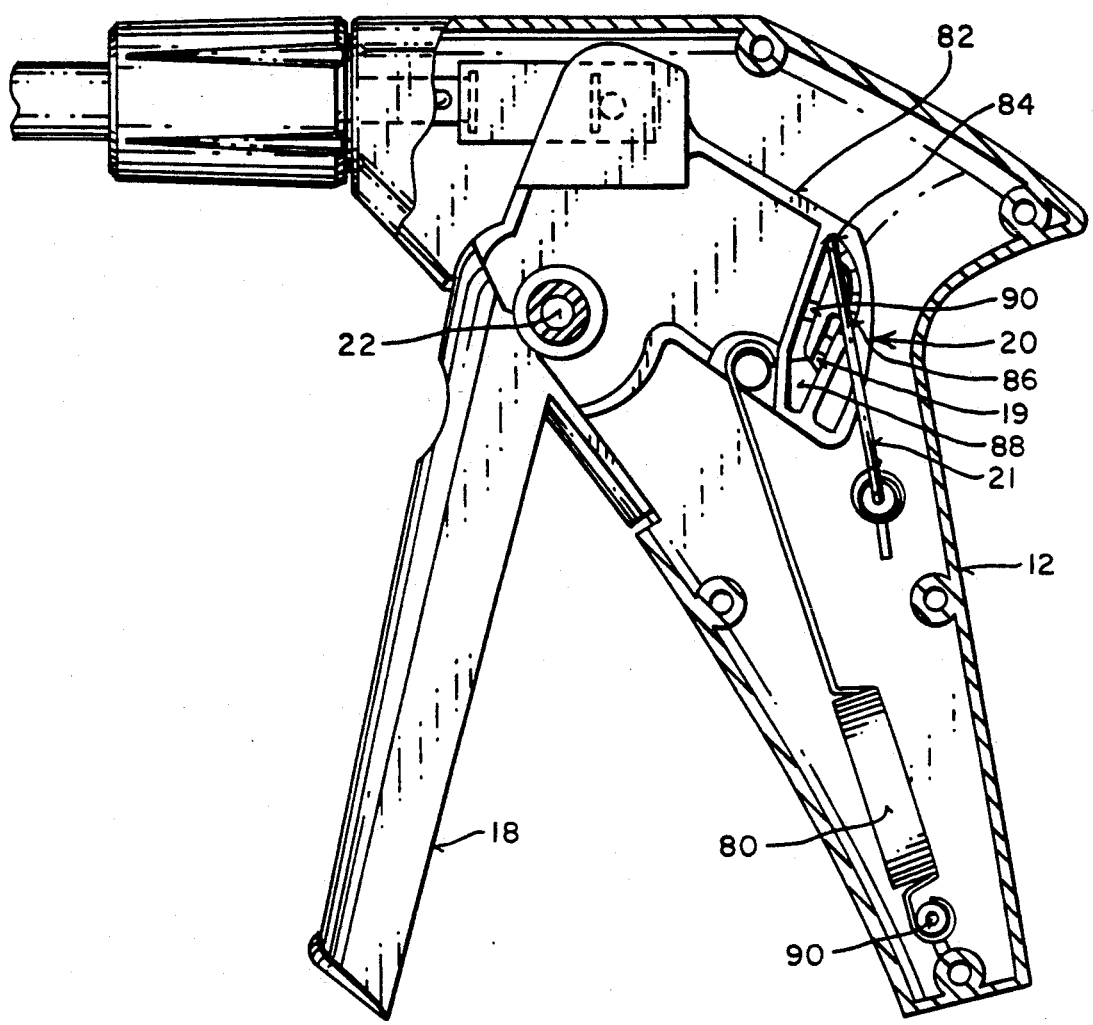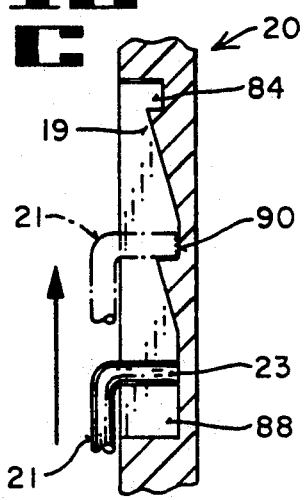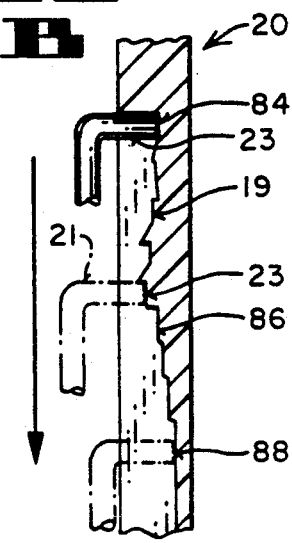

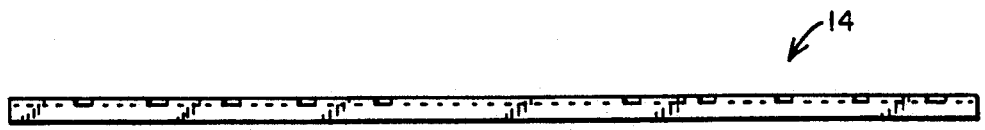
FIG _ 11A
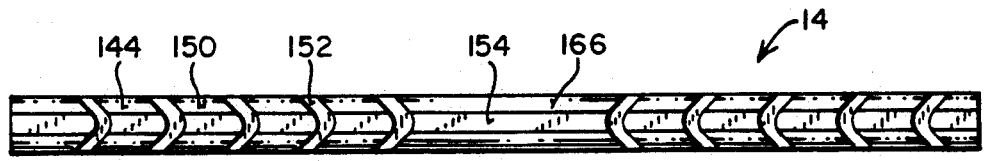
FIG _ 11B
FIG _ 11C
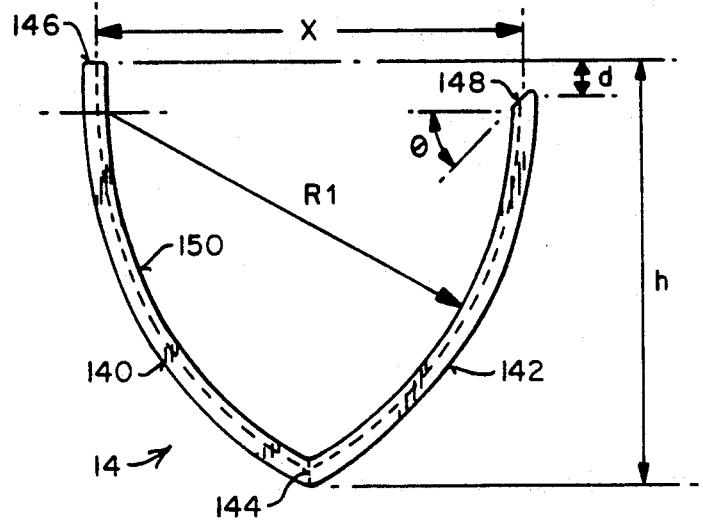
FIG 11D
FIG 11E
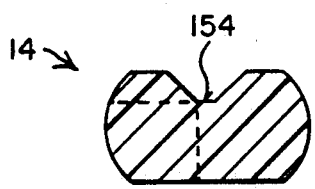
FIG _ 11F
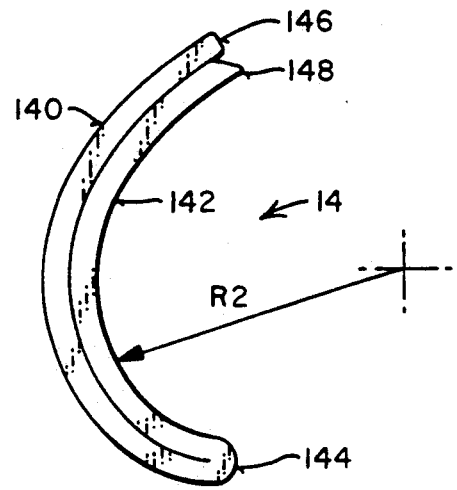

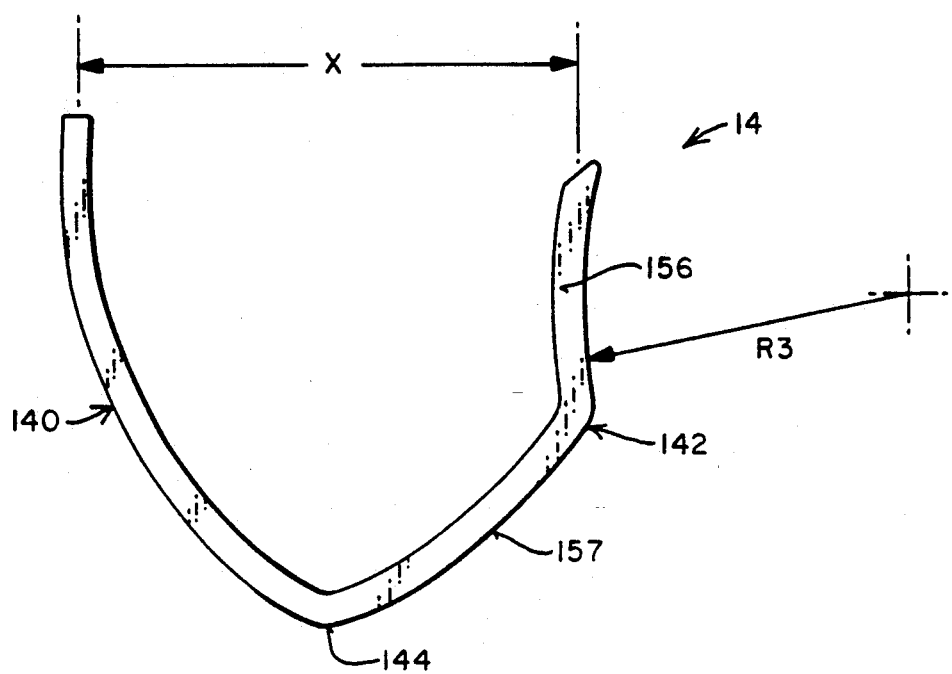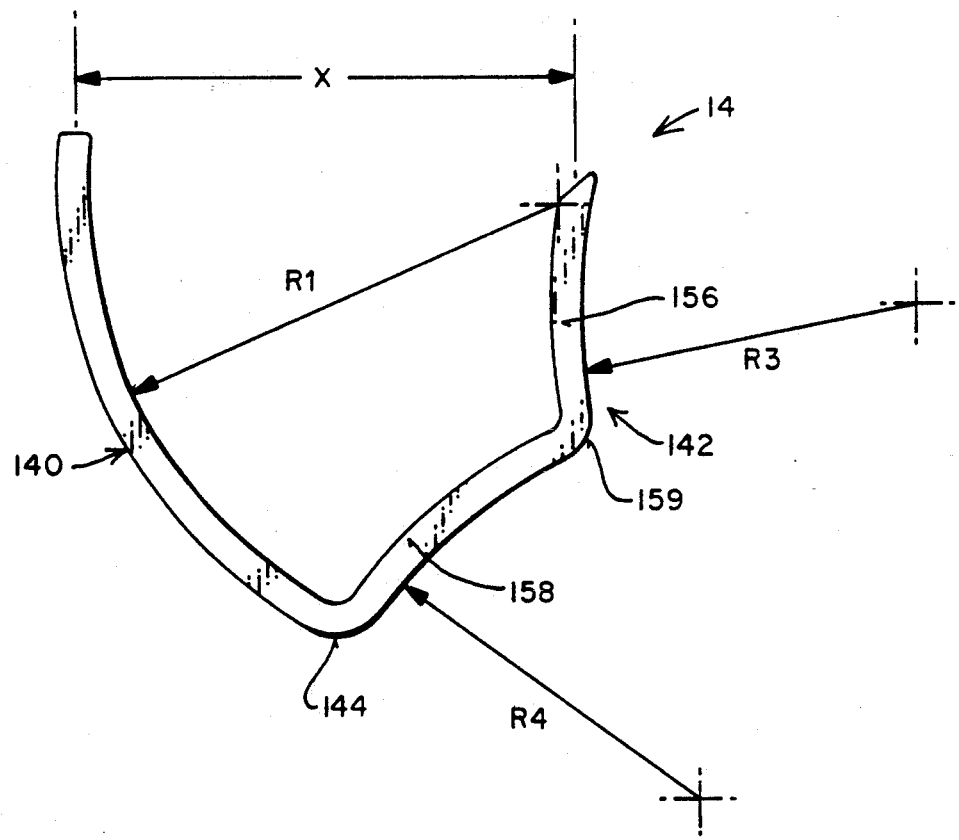

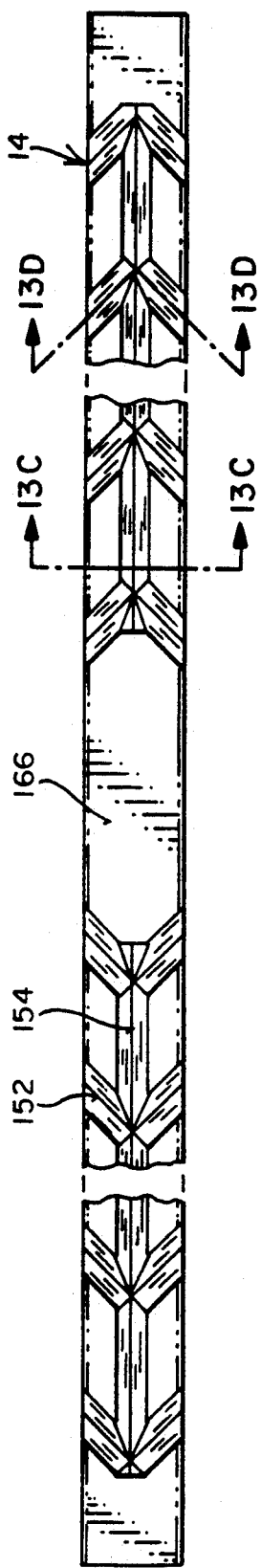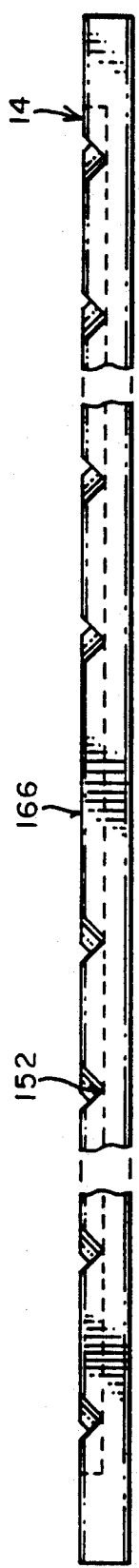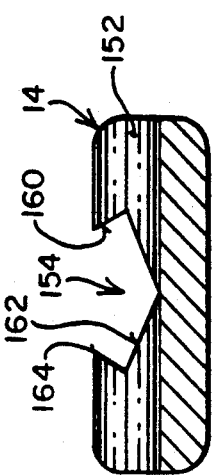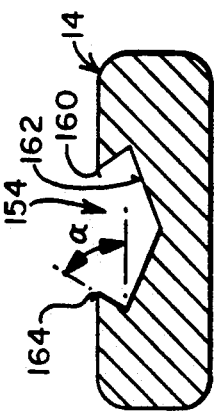

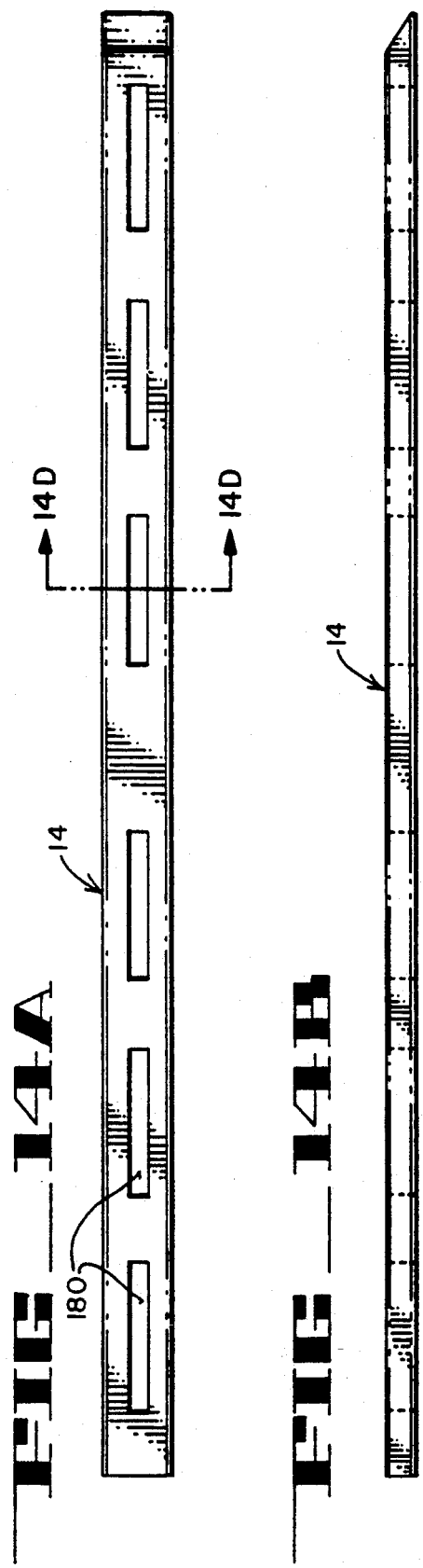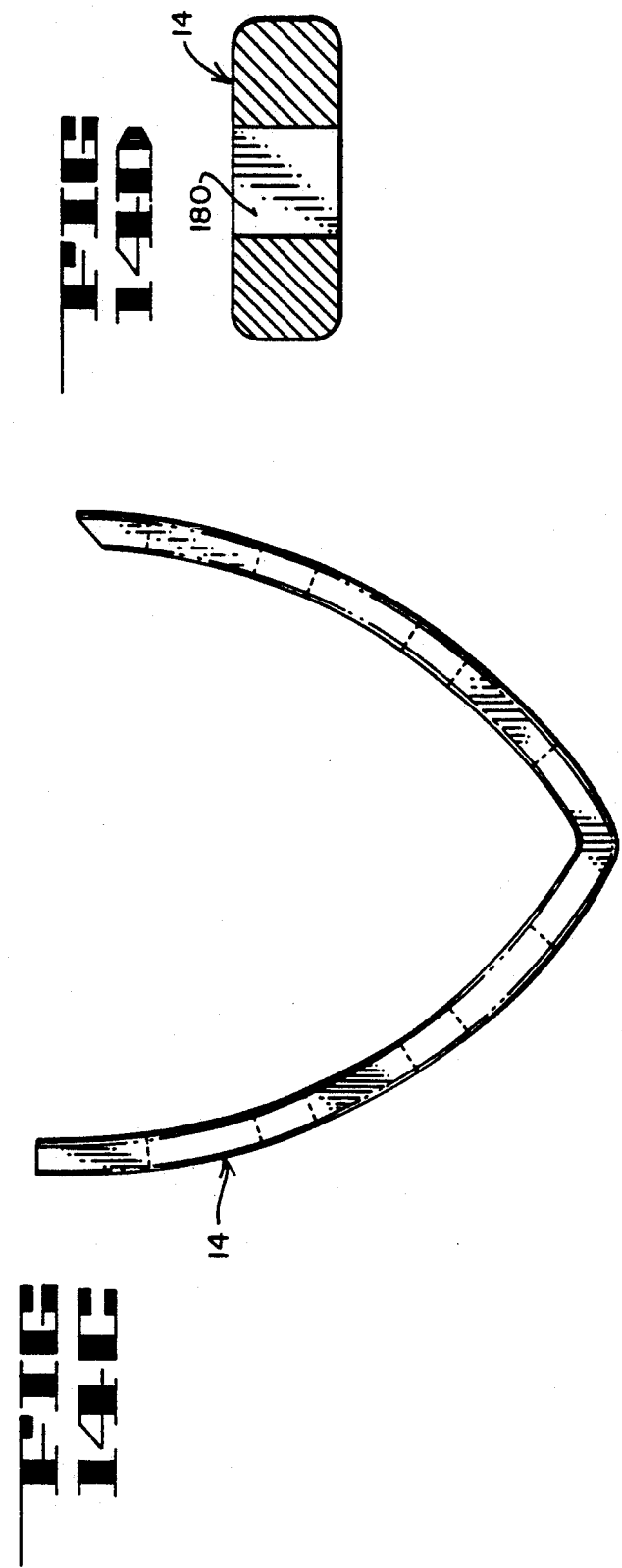
FIG_14A
FIG_14B
FIG_14C
FIG_14D

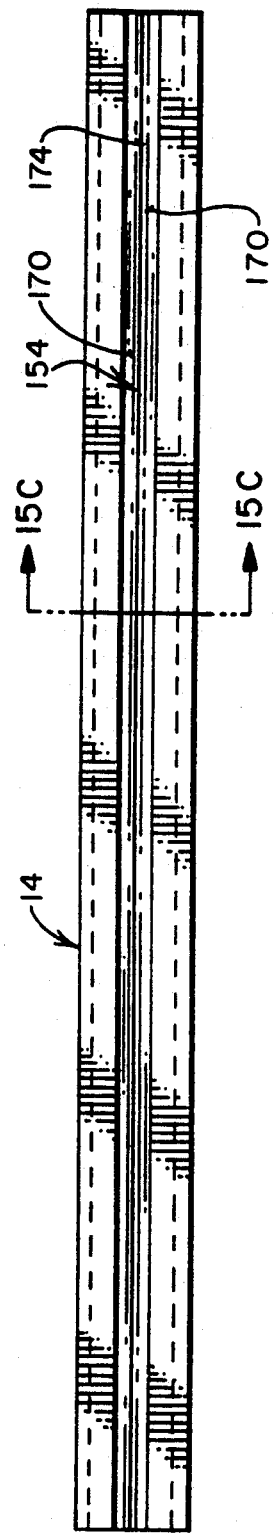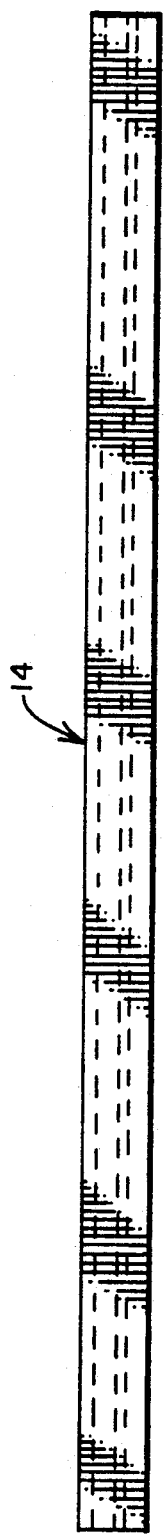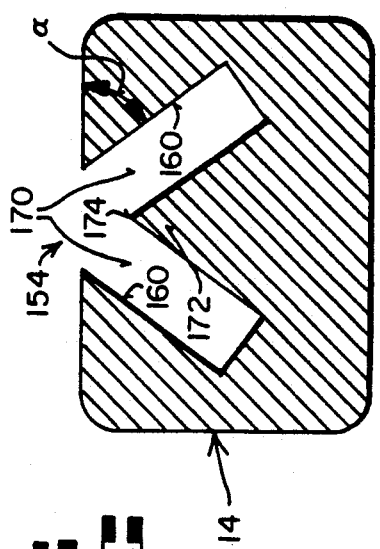
FIG_15A  FIG_15B  FIG_15C

SURGICAL CLIP

CROSS-REFERENCE TO RELATED APPLICATION

This is a continuation in part of U.S. application Ser. No. 07/908,709, filed Jul. 2, 1992, now abandoned, entitled "Surgical Clip," which is a continuation-in-part of U.S. application Ser. No. 07/888,723, filed May 26, 1992, now U.S. Pat. No. 5,192,288, entitled "Surgical Clip Applier". The full disclosures of both patents are incorporated herein by reference.

BACKGROUND OF THE INVENTION

The present invention relates generally to surgical instruments and more specifically to surgical clips used in surgical clip appliers for ligating blood vessels and other tubular ducts or tissue.

In surgical procedures, it is frequently necessary to ligate ducts, such as blood vessels, or other severed tissue. For this purpose, it is well-known to use surgical clip appliers, such as that described in U.S. Pat. No. 3,439,522, to apply surgical clips to a duct or tissue to be ligated. Such clip appliers typically have a scissor-like construction, with a pair of movable handles which are grasped by the surgeon, and a pair of movable jaws opposite the handles into which a surgical clip is placed. Surgical clips usually have a pair of connected legs to form a U or V shape. When the handles are closed, the jaws close the legs of the clip together on the vessel or other tissue to be ligated.

In some surgical procedures, it is desirable to use a clip applier which is configured to allow tissue ligation in inaccessible areas of the surgical site. To address this need, a number of surgical clip appliers have been developed with the jaws extended a distance from the handles, or with the jaws oriented at various angles. Examples are described in U.S. Pat. Nos. 3,777,538, and 4,440,170.

Other known clip appliers, such as that described in U.S. Pat. No. 4,616,650, provide for retaining multiple clips in the applier and feeding the clips toward the distal end of the applier, thereby permitting the surgeon to apply multiple clips at various places in the surgical site without removing the clip applier from the site to place another clip in the jaws. In some of these known devices, the clip applier is designed to accommodate an interchangeable cartridge containing multiple clips. An example is seen in U.S. Pat. No. 3,675,688.

Other clip appliers have been developed for use in laparoscopic surgical procedures. Laparoscopic procedures usually involve distending the abdominal cavity away from the underlying organs to improve access and visibility, using gas insufflation or a mechanical distension technique. Several small incisions are made in the abdomen through which are inserted trocar sleeves—plastic tubes designed to provide a sealed entryway into the abdominal cavity. Surgery is performed using long-handled instruments inserted through the trocar sleeves, with a lens connected to a video monitor providing visibility of the abdominal cavity.

The parent to this application describes a clip applier having particular usefulness in laparoscopic surgery. The clip applier includes an elongated shaft mounted to a handle, with a movable belt disposed in the shaft having a plurality of retainers for holding clips. An anvil is mounted at the distal end of the shaft and a hammer is movable against the anvil by actuating a lever mounted to the handle. A unique feature of the clip applier is the feeding of the clips on the belt with the legs pointing distally, then rotating the clips so that the legs point laterally in the anvil. Also unique is the curved shape of the anvil and the distal end of the hammer, which form the legs of the clip in a curved and parallel configuration when the clip is closed. It has been found that this curved configuration results in improved gripping force on the tissue to which the clip is applied, and permits the amount of clip surface available for gripping tissue to be maximized relative to the size of the clip.

Various types of surgical clips have been developed for use in clip appliers like the forementioned. However, it has been found that known surgical clips suffer from certain disadvantages. First, known surgical clips are not suitable for use in a clip applier which closes clips in a curved shape, like that described in the parent to this application. Because known clips generally have two legs of the same length, if such clips are formed in a curve when closed, the tip of one leg (on the inside of the curve) will extend beyond the tip of the other leg (on the outside of the curve). This effectively reduces the amount of surface area of the clip available for gripping tissue, reducing its effectiveness.

Known surgical clips further suffer from undesirably low reliability in remaining properly secured to the desired tissue area. Several factors contribute to this problem, including the tendency of the clip legs to spread apart due to their inherent resiliency, as well as inadequate grip between the clip surfaces and the tissue to which the clip is applied.

In addition, known surgical clips have an undesirably small area of clip surface available for gripping tissue relative to the overall size of the clip. This is especially significant in laparoscopy, where the clip applier with clips retained therein must be inserted through a trocar sleeve of limited size. Such sleeves commonly have a diameter of 10 mm. A clip applier and clip must be designed to be inserted through such a sleeve, while at the same time maximizing the area of the gripping surface of the clip. If it is desired to use a clip applier for applying clips in a lateral, rather than distal direction, clip size is particularly limited, since the laterally-facing jaws for closing the clips must be small enough to fit through the trocar sleeve, thereby limiting the height of the clips. Known clips suitable for lateral application which are insertable through a 10 Mm trocar sleeve have incorporated geometries which have limited the surface area available for gripping.

For these and other reasons, a surgical clip is desired which can be closed in a curved configuration, and which has improved reliability in remaining secured to tissue. Preferably, the clip could be used in conjunction with a variety of clip appliers, including those with distally-facing jaws, those with laterally-facing jaws, those employing cartridges for holding multiple clips, and those having belt-type feed mechanisms. The surgical clip should have improved gripping surfaces as well as tighter closure between the legs to ensure security on the tissue to which the clip is applied. The clip should further provide a large area of gripping surface relative to the overall size of the clip.

SUMMARY OF THE INVENTION

The present invention provides a surgical clip for use in a clip applier which can be closed in a curved configuration, has improved tissue gripping reliability, and maximizes the gripping surface for a given clip size.

In one embodiment, the surgical clip comprises a first leg and a second leg connected at an apex to generally form a V-shape. A channel extends longitudinally along the gripping surfaces of each leg, which is sometimes intersected by a plurality of transverse grooves. The channel preferably has at least one undercut sidewall, such that the distance between the channel sidewalls width of the channel at an interior portion of the channel is wider than the width at its open side at the gripping surface. Such a channel configuration has been found to result in significantly improved grip on tissue to which the clip is applied.

In a specific embodiment, a pair of inclined channels extend longitudinally along the gripping surfaces of the legs. The inclined channels slope outwardly as they extend into the clip from the gripping surface. The inclined channels intersect near the gripping surface of the clip, forming an opening at the gripping surface that is wider than each of the inclined channels individually.

In another embodiment, a first of the clip legs is longer than a second leg by a distance selected so that the ends of the legs are substantially even when the clip is closed in a curved shape. This permits the clip to be applied by a clip applier which closes the clip in a curve, thereby gaining the benefits of improved grip and larger gripping area which such a curve has been found to produce.

In still another embodiment, the clip legs have a curvature selected so that the gripping surface of each leg is at least partially concave. This produces a clip with an overall height from the ends of the legs to the apex which is small relative to the surface area available for gripping tissue. The gripping surface of the clip is thereby maximized for a given clip size, making the present invention particularly advantageous for use in laparoscopic surgery.

The surgical clip of the present invention further improves clip grip by providing tighter closure of the clip legs. In a preferred embodiment, this is accomplished by providing at least one of the legs with a distal portion having a curvature in the opposite direction as the proximal portion of the leg. Such a reverse curvature counteracts the resiliency in the legs which causes spreading in known clips.

A further understanding of the nature and advantages of the invention may be realized by reference to the remaining portions of the specification and the drawings.

DESCRIPTION OF THE DRAWINGS

FIG. 1 is a perspective view of a clip applier constructed in accordance with the principles of the present invention.

FIGS. 2A and 2B are front and top cross-sectional views of the clip applier of FIG. 1 before a clip has been advanced into the anvil.

FIGS. 3A and 3B are front and top cross-sectional views of the clip applier of FIG. 1A with a clip in position in the anvil before closing.

FIGS. 4A and 4B are front and top cross-sectional views of the clip applier of FIG. 1A wherein a clip has been closed in the anvil.

FIGS. 5A-5C are close-up front cross-sectional views of the distal end of the clip applier of FIG. 1A showing a clip prior to being advanced into the anvil, in position in the anvil before closing, and in a closed position in the anvil, respectively.

FIGS. 6A and 6B are front and top cross-sectional views of the distal end of the clip applier of FIG. 1A.

FIG. 7 is a perspective view of the whip of the clip applier of FIG. 1A.

FIG. 8 is a perspective assembly view of the distal end of the clip applier of FIG. 1A.

FIGS. 9A and 9B are front and top cross-sectional views of the proximal end of the barrel of the clip applier of FIG. 1.

FIG. 10A is a front and side cross-sectional views of the handle of the clip applier.

FIGS. 10B and 10C are side cut-away views of the ratchet mechanism in the handle of FIG. 10A.

FIGS. 11A and 11B are front and top elevational views of a surgical clip constructed in accordance with the principles of the present invention with legs straightened to illustrate surface features.

FIGS. 11C-11E are front and side elevational and side cross-sectional views of the surgical clip of FIGS. 11A and 11B in an unclosed configuration.

FIG. 11F is a front elevational view of the surgical clip of FIGS. 11A and 11B in a closed configuration.

FIGS. 12A and 12B are front elevational views of alternate embodiments of a surgical clip constructed in accordance with the principles of the present invention.

FIGS. 13A and 13B are top and front elevational views of a further embodiment of a clip constructed in accordance with the principles of the present invention.

FIGS. 13C and 13D are transverse cross-sectional views of the clip of FIGS. 13A and 13B.

FIGS. 14A-14C are front and top elevational views of a further embodiment of a clip constructed in accordance with the principles of the present invention.

FIG. 14D is a transverse cross-sectional view of the clip of FIGS. 14A-C.

FIGS. 15A and 15B are top and front elevational views of a further embodiment of a surgical clip constructed in accordance with the principles of the present invention.

FIG. 15C is a transverse cross-sectional view of the surgical clip of FIGS. 15A-15B.

DESCRIPTION OF SPECIFIC EMBODIMENTS

Referring to FIG. 1, the surgical clip applier of the present invention includes, in a preferred embodiment, a tubular shaft or barrel 10 rotatably coupled to a handle 12, the barrel 10 holding a number of surgical clips (not shown) oriented in the barrel such that clip legs point toward the distal end of the barrel, as will be described in detail below. An anvil 16 is disposed at the distal end of the barrel and forms a slot having an open side facing laterally from the barrel. In a preferred embodiment, the slot in anvil 16 is oriented at 90° relative to the barrel 10. However, it should be understood that the slot may be configured at any of various angles from 5° up to approximately 170° relative to barrel 10.

Referring now to FIG. 2A, a lever 18 is pivotally mounted to handle 12 at pivot point 22 and includes a ratcheting mechanism 20 including a grooved track 19 and a pawl 21 following track 20. As shown in FIGS. 3A and 3B, when lever 18 is pulled toward handle 12, the distal-most clip 24 is positioned in the anvil 16 with legs 15 pointing laterally. At the same time, pawl 21 has advanced in track 20 reaching an intermediate rest position as will be described more fully below.

As shown in FIGS. 4A and 4B, when the lever 18 is pulled to a position nearest handle 12, distal-most clip 24 is closed against anvil 16 by hammer 26 which extends from the interior of barrel 10.

The three major stages of closing distal-most clip 24 are shown in detail in FIGS. 5A through 5C. In FIG. 5A, distal-most clip 24 is in a position at the distal end of the barrel 10 with legs 15 pointing distally. The distal end of hammer 26 is in a position toward the proximal end of the barrel relative to clip 24. In the position of FIG. 5B, lever 18 has been pulled toward handle 12 and hammer 26 has been translated distally, pushing on clip 24 to rotate the clip along the curved track 28 of anvil 16, so that legs 15 of the clip 24 are oriented in a lateral direction. In FIG. 5C, lever 18 has been pulled to the fullest proximal position, translating hammer 26 further distally, closing the clip 24 against track 28 of anvil 16.

The construction of the distal portion of the barrel of the clip applier is illustrated in FIGS. 6A and 6B. Clips 14 are retained in retainers 32 on belt 30. The belt 30 is composed of a flexible material, for example, molded plastic, or a metal such as nickel, and is sufficiently rigid to carry clips 14 without deforming away from the surface of belt track 36. In an exemplary embodiment, belt 30 is electroformed nickel with a thickness of 0.001"–0.002". Retainers 32 have a short distal portion separable from a longer proximal portion by a distance equal to or slightly less than the thickness of clips 14 at apex 17. Apex 17 fits snugly between the distal and proximal portions of retainer 32. Belt 30 is disposed on belt track 36 having rounded ends 37 about which belt 30 is rotatable. Clips 14 are guided in clip space 34 adjacent belt 30, shown in FIG. 6B. Clips 14 are advanced in a distal direction along barrel 10 by movement of belt 30 around belt track 36. The belt is advanced by belt puller 38, which engages and pulls empty retainers 32 in a proximal direction on the non-clip-carrying side of the belt 30.

Clips advanced by belt 30 along clip space 34 encounter whip 40 at the distal end of clip space 34. Typically, whip 40 is made of sheet metal or other smooth, hard and resilient material. Whip 40, as illustrated in FIG. 7, has a first surface 42 parallel to the belt and situated so as to lie between the belt and the distal-most clip retained thereon. As the clip advances further distally, the legs of the clip encounter ramp 43 which guides the legs 15 of the clip out of the plane in which the clips are carried on belt 30. At this point, the apex 17 of clip 24 is still retained in retainer 32. As the belt continues to advance, legs 15 move up ramp 43 and apex 15 is forced out of retainer 32, the clip being left in a position with legs 15 against ridge 46 of whip 40.

It can be seen that, in a preferred embodiment, clips are fed on belt 30 in clip space 34, which is disposed laterally of the central axis of barrel 10. On the other hand, in order to optimize loading when the clip is closed, hammer 26 is disposed in the center of barrel 10 and is translated along the central axis. Whip 40 transfers clips from the offset path of feeding to a central position for engagement by hammer 26 and closing against anvil 16. This configuration maximizes the use of space within barrel 10, which is designed to be insertable through a 10 mm trocar sleeve, while optimizing loading through the clip applier when the clips are closed.

Support 48 of whip 40 rests against the inner surface of tube half 50b of barrel 10, and provides resilient support for the distal end of whip 40. A guide arm 45 extends from the distal end of the whip for engaging a lower leg 15b of a clip (FIG. 6A) as it is advanced into the anvil, thereby ensuring leg 15b is guided into track 28.

Once distal-most clip 24 is on surface 49 of whip 40, it is in a position for engagement by hammer 26. The distal end 27 of hammer 26 pushes on apex 17 of clip 24, forcing clip 24 over ridge 46 of whip 40. Support 48 of whip 40 allows whip 40 to resiliently give way as the clip 24 is pushed over ridge 46 by hammer 26. Ridge 46 is configured in a shape complementary to that of clips 14 so as to align clip 24 with legs 15 pointing symmetrically in the distal direction as the clip is advanced distally.

As clip 24 is pushed distally, outer leg 15a, shown in FIG. 6A, engages stop 52 at the distal end of barrel 10. Stop 52 obstructs movement of leg 15a, while leg 15b continues to move distally under the force of hammer 26. Leg 15b rotates about stop 52 and is guided by portions of guide arm 45 of the whip and track 28 in anvil 16 until the clip is in the position shown in FIG. 3A or 5B. Further distal movement of hammer 26 pushes leg 15a over stop 52 and toward leg 15b.

Track 28 in anvil 16 is usually curved from the bottom of the slot to the end point 54 of the track. Track 28 is further recessed in anvil 16 to allow clips to be rotated into the anvil without interfering with tissue positioned therein. The distal end 27 of hammer 26 is of a shape conforming to the shape of track 28 in anvil 16. As the hammer closes the clip, legs 15a and 15b are formed into the shape of track 28 and distal end 27, leaving legs 15a and 15b in a curved configuration when the clip is closed, as shown in FIG. 5C.

By closing the clip in such a curve, several benefits are obtained. First, clips closed on tissue in such a curved shape have been found to have improved grip over clips closed with the legs straight. Second, by using a curved hammer and anvil, the size of the clip applier relative to size of clips it can apply is minimized. Thus, the clip applier can be designed to be insertable through a 10 mm trocar sleeve while accommodating clips with longer legs than those which clip appliers with straight-leg closure can accommodate if designed for a trocar of similar size. The clip applier of the present invention, designed for a 10 mm trocar sleeve, is preferably capable of applying clips with legs at least 0.250 inches in length, from the apex of the clip to the tip of the shortest leg along the gripping surface.

The manner of rotating clips in the clip applier of the present invention is of particular importance. As seen in FIGS. 6A–6B, clip 24 rotates about stop 52 with leg 15b in track 28. The axis of clip rotation can lie anywhere in the area between and including the legs of the clip, the axis being perpendicular to the plane in which the clip lies. This allows a clip to be rotated from a distal orientation in the barrel 10 to a lateral orientation in anvil 16 without substantially entering the space in the slot of anvil 16. Thus, if the slot is positioned about a piece of tissue or duct, it need not be removed in order to rotate a clip into position in the anvil for closing. The clip can rotate into position without interference with tissue in the slot.

The assembly of the various components of barrel 10 is illustrated in FIG. 8. A pair of opposing tube halves 50a, 50b extend from the handle 12 to the anvil 16. Flange 74 at the proximal end of the tube halves is rotatably coupled to the handle as described below. Preferably tube halves 50a, 50b are a translucent plastic which provides rigidity to the barrel and permits the interior components of the barrel to be visible. The interior surfaces 51a, 51b of tube halves 50a, 50b are configured to form several channels in which the components of the barrel are nested. Tube halves 50a, 50b are preferably fastened to each other via tabs (not shown) along their longitudinal adjoining edges. Alternatively, adhesive or ultrasonic welding may be used to bond the halves 50a, 50b together.

Belt puller 38 is disposed between right tube half 50a and belt 30, belt 30 being disposed about belt track 36. Belt puller 38 has a proximal portion parallel to and separated from belt 30 by a gap so as not to interfere with belt movement. Near the distal end of belt puller 38 a raised portion 100 extends into a plane immediately adjacent belt 30. Raised portion 100 has a cutout section 102 from which a leg 104 is bent away from the surface of raised portion 100 and toward right tube half 50b. Tooth 106 at the distal end of cutout 102 is angled toward the surface of belt 30, preferably at about 20°, so as to engage retainers 32 when the belt puller moves in a proximal direction, but to ride over retainers 32 when the belt puller moves in a distal direction. Distal end 108 of belt puller 38 extends from the raised portion 100 back toward tube half 50b, distal end 108 and leg 104 providing resilient supports to maintain the position of raised portion 100 and tooth 106 immediately adjacent belt 30.

Clips 14 are carried by belt 30 in retainers 32 on the side of belt track 36 opposite that engaged by belt puller 38. The tips of clip legs 15 are guided by the interior surface 51b of tube half 50b forming clip space 34. Whip 40 is disposed in a position such that planar portion 42 lies between clips 14 and belt 30 at the distal end of belt track 36.

Clip wall 110 is disposed adjacent belt 30 and parallel thereto to provide a surface to retain clips 14 in position and guide them to the distal end of the barrel without interference from the other components in barrel 10. Hammer 26 coupled to a hammer extension 56 is disposed adjacent clip wall 110. Distal end 27 of hammer 26 has a groove 112 slightly wider than the width of clips 14 for greater precision and reliability in engaging the clips. The proximal end 114 of hammer 26 is of a reduced thickness to fit within slot 116 at the distal end of hammer extension 56 to which it is fixed by welding or other known means. Hammer extension 56 has a longitudinal rib 118 providing increased rigidity. A flange 68 at the proximal end is coupled to the handle as described below. Hammer 26 is disposed in a position such that groove 112 in distal end 27 engages clips residing on surface 44 of whip 40 when hammer extension 56 and hammer 26 are extended distally.

Structural members 120, 122 are disposed adjacent hammer 26 and hammer extension 56. Left structural member 122 has a longitudinal rib 124 providing rigidity thereto, and is welded to structural member 120. Structural members 120, 122 are fastened to left tube half 50a via pins 127 extending from left tube half 50a and inserted through holes 126, the pins being secured by heating and flattening the ends or by other known means.

Anvil 16 has an extension 128 which fits between tube halves 50a, 50b and is usually welded to one of structural member 120, 122. Extension 128 has a channel 130 into which belt track 36, belt 30 and whip 40 extend. Thus, when a clip 24 is disengaged from belt 30 by ramp 43 of whip 40, the clip resides on surface 44 with legs 15 within channel 130 of anvil 16. As hammer 26 pushes a clip 24 from whip 40 toward the anvil, the lower clip leg 15b engages track 28 in anvil 16 which guides the clip through its rotational motion.

Referring now to FIGS. 9A and 9B, the proximal end of the barrel 10 will be more fully described. Barrel 10 is rotatably fixed to handle 12 by collar 70 having an internal cylindrical aperture 72 for trapping flange 74 at the proximal end of barrel 10. A rotation knob 75 is disposed around collar 70 and engages features 76 on the exterior of tube halves 50a, 50b, permitting the barrel 10 to be rotated by the user from a point near the handle and outside the surgical site.

Tube halves 50a, 50b extend into collar 70 of handle 12, with flange 74 being engaged in aperture 72, as shown in FIG. 9A. Belt track 36, belt 30, clip wall 110 and left tube structure 122 terminate at a point distally of aperture 72 in collar 70. Right structural member 120, fastened to left structural member 122 and left tube half 50a, extends into collar 70 and is formed at a right angle into flange 74 of tube half 50a so as to rotate therewith.

Actuation of the hammer 26 at the distal end of the barrel 10 is accomplished by hammer extension 56 coupled to hammer 26 and extending from the hammer's proximal end to link 58 in handle 12. Link 58 has a proximal portion 59 pivotally coupled to handle 18 by pin 62 disposed in slot 60 of link 58. The distal portion 64 of link 58 has a cylindrical aperture 66 in which flange 68 of hammer extension 56 is trapped. This configuration permits hammer extension 56 to be rotated with barrel 10.

Belt puller 38, as shown in FIG. 9B, extends from the distal portion of the barrel 10 parallel to the surface of the belt 30 and, at a point proximally of the proximal end of clip wall 110, fastens to hammer extension 56 by welding or other known means. Thus, belt puller 38 acts in unison with hammer extension 56 according to the position of lever 18.

In an exemplary embodiment, collar 70, aperture 66 in link 58 and the body of handle 12 are configured with an openable exterior structure so as to permit barrel 10 to be removed from handle 12, allowing barrels to be interchanged with a single handle.

In operation, when lever 18 is in the position shown in FIG. 2A, link 58 is in its most proximal position, as are hammer extension 56, hammer 26, and belt puller 38. As lever 18 is pulled toward handle 12, link 58 is moved in a distal direction thereby pushing hammer extension 56 distally, pushing hammer 26 against clip 24 and placing it in the position shown in FIG. 2B. Further movement of lever 18 toward handle 12 moves link 58, hammer extension 56 and hammer 26 further distally, thereby closing the distal-most clip 24 as in FIG. 2C. As lever 18 is then returned to its original position, link 58 is pulled in the proximal direction, pulling both hammer 26 and belt puller 38 in the proximal direction. Belt puller 38 engages retainers 32 on belt 30, as described above, thereby pulling the non-clip-carrying side of the belt 30 in the proximal direction, with the clip-carrying side of the belt 30 on which clips 14 are retained being advanced in the distal direction. In this manner the steps of advancing the clips in the barrel, positioning the distal-most clip in the anvil, and closing the distal-most clip are all performed by actuating a single lever on handle 12.

Referring to FIGS. 10A-10C, the ratcheting feature of the invention will now be described. Within handle 12, lever 18 has a ratcheting mechanism 20 including a grooved path 19 and a pawl 21 following grooved path 19. Pawl 21 is laterally flexible and resilient so as to follow the contours of path 19, while having compressive strength to prevent movement of lever 18 in the reverse direction. Grooved path 19 has a contour as shown in FIGS. 10B and 10C, including a series of sloping sections terminating in vertical cliffs. Pawl 21 has a hooked end portion 23 which follows the contour of grooved path 19, being guided up the successive ridges and over each cliff. When handle 18 is in its fully outward position such that clips 14 and hammer 26 are in the positions shown in FIGS. 2A and 5A, hook 23 of pawl 21 is at point 84 of FIGS. 10B and 10C. As lever 18 is moved toward handle 12, hook 23 follows the ridge from point 84 and over a cliff at point 86 as shown in FIG. 10B. Point 86 corresponds to the position of FIGS. 3A and 5B. As lever 18 is further moved toward handle 12, hook 23 is moved to position 88, corresponding to FIGS. 4A and 5C.

A spring 80 between arm 82 of lever 18 and anchor point 90 of handle 12 allows lever 18 to return to its original position simply by releasing pressure. Referring to FIG. 10C, as lever 18 returns, hook 23 of pawl 21 moves from point 88 over a cliff to point 90 and then over a second cliff back to point 84.

It should be evident that the ratcheting mechanism as described prevents the return of lever 18 to its outward position when a clip has been positioned in the anvil before closing, as in FIGS. 3A or 5B, or midway through the closing action. This prevents more than one clip from being fed to the anvil at any one time, which could jam the device. Further, it permits the user to move a clip into position in the anvil before closing, as in FIGS. 3A and 5B, and release pressure on the lever 18 while the clip in anvil 16 is positioned around the duct or tissue to be ligated, without returning hammer 26 to its proximal position or advancing belt 30.

An additional feature of the invention is an indicator for indicating to the user that the barrel of the clip applier contains no more clips. In a preferred embodiment, the indicator comprises a feature on belt 30 similar to retainers 32 which stands a greater height from the surface of belt 30 than do retainers 32. Referring to FIG. 6B, when the raised feature (not shown) carried by belt 30 encounters stop 92 in tube half 50b, the raised feature is unable to proceed further, thereby stopping the belt from movement. This prevents lever 18 from returning to its released, outward position, leaving the lever in a position between fully-released and fully-depressed. This will signal to the user that all of the clips in barrel 10 have been applied. An unknowing user, however, might at this point attempt to pull lever 18 toward handle 12 in an effort to make lever 18 return to its fully-released position. For this reason, the cliff at point 90 in the ratcheting mechanism 20 as described above is provided. When the belt 30 is prevented from movement by the raised feature, hook 23 on pawl 21 will have traveled from position 88 in grooved path 82 over the cliff at point 90, but lever 18 will be unable to move further, leaving pawl 21 at point 90. In the absence of a cliff at point 90, the user could pull lever 18 toward handle 12 moving pawl 21 back into position 88, potentially jamming the device and/or confusing the user. Therefore, the cliff at point 90 ensures that when the raised feature on belt 30 has stopped the return movement of lever 18, no additional movement of lever 18 in either direction is possible.

Referring now to FIGS. 11A-E, 12A-B and 13A-D, the surgical clip of the present invention will be described. In a preferred embodiment, the surgical clip comprises a pair of arched legs 140, 142, connected by an apex 144. Long leg 140 is longer than short leg 142 by a distance d, which, in one embodiment, is preferably about 0.025 inches where the distance h from the apex to the end of long leg 140 is about 0.28 inches. The gap x between distal tips of legs 140, 142 is preferably in the range of 0.280 to 0.310 inches for use with a 10 mm trocar sleeve, but could be larger or smaller depending upon the size of the sleeve used. The legs are arched in a curvature having a radius R1, which is preferably in the range of 0.200 to 0.500 inches, preferably about 0.265 inches, with at least a portion of the gripping surface 150 of the legs concave.

By configuring the clip 14 with a longer leg 140, both legs of the clip can be formed into a curve conforming to that of anvil 16 and clip track 28, such that both legs in the closed configuration are parallel and tips 146, 148 are substantially even, as shown in FIG. 11F. Preferably, the closed clip is curved at a radius R2 in the range of 0.200 to 0.500 inches.

In a further embodiment, short leg 142 is cut at its distal tip 148 at an angle $\theta$ in a range of 10° to 85°, preferably about 45°. As illustrated in FIGS. 5A-5C and 6A, this angular feature serves to allow leg 142 (identified as leg 15a in FIG. 6A) to pass over stop 52 at the distal end of barrel in a continuous and controlled manner when leg 142 (15a) of clip 24 is pushed distally by hammer 26.

In a further preferred embodiment, the clip gripping surface 150 has surface features for improving the grip of the clip on tissue. Preferably, the surface features comprise a longitudinal channel 154 and a plurality of transverse grooves 152 for improving the grip of clip 14 on tissue. Preferably, the surface features 152 comprise curved or angled grooves, as shown in FIG. 11B, extending from one edge of the clip to the other. Usually, a region 166 near apex 144 is substantially free of surface features. In one embodiment, the features extend to a depth of about ⅓ the thickness of the clip. In other embodiments, the surface features may comprise slots or holes of various shapes and densities, drilled at various depths into clip 14, including completely through the thickness of the clip, as illustrated in FIGS. 14A-D. In FIGS. 14A-14D, the surface features comprise rectangular or oval-shaped slots 180, drilled through the thickness of the clip 14. Slots 180 may be of various sizes, shapes and patterns as required for particular procedures.

Preferably, channel 154 has at least one sidewall 160 which is undercut so that the width of the channel across floor 162 is greater than the width across the opening 164 at the gripping surface of the clip, as illustrated in FIGS. 13A-D. The clip is shown with legs straightened for purposes of clarity, but usually is formed with arched legs as shown in FIGS. 11C or 12A-B. The undercut on sidewall 160 provides improved grip, due to the tendency of tissue to be forced into the undercut when the clip is applied. The undercut exerts a vertical retention force on the tissue beneath it. Preferably, the sidewall is inclined at an angle $\alpha$ in the range of 60°-88°. Transverse features 152 may further be provided with undercut sidewalls as described with respect to channel 154.

In one embodiment, channel 154 and/or transverse features 152 may be formed using laser drilling. Such a process produces a burn pocket at the base of the channel which is wider than the channel opening at the surface of the clip. The undercut sidewall 160 thereby results without additional machining.

In other embodiments, channel 154 may have arcuate or inclined sidewalls with the width at the opening 164 larger than that at the floor 162, as shown in FIG. 11E. Floor 162 is preferably concave, either with sloping surfaces (FIGS. 13C, 13D) or with an arcuate surface. Channel 154 may extend the full length of the clip, as shown in FIG. 11B, or only over the gripping surfaces or portions thereof, as in FIGS. 13A and 13B.

A further embodiment of the clip of the present invention is illustrated in FIGS. 15A-15C (clip shown straightened for clarity). In this embodiment, channel 154 includes a pair of inclined channels 170 which have inclined sidewalls 160. The inclined channels will be inclined at an angle $\alpha$, preferably in the range of 60° to 88°. Inclined channels 154 intersect near the gripping surface, forming an opening at the gripping surface which is wider than the width of either channel by itself. Between the inclined channels is a triangular base 172 having an apex 174 disposed centrally below the opening in the gripping surface. Such inclined channels may form not only a longitudinal channel in the gripping surface as shown in FIGS. 15A-15C, but transverse grooves as well, such as those shown in FIG. 13.

Alternative clip embodiments are illustrated in FIGS. 12A-12B. These embodiments take advantage of plastic and elastic deformation characteristics of the clip legs to achieve tighter closure. It has been found that in closing the clip, certain portions of the legs undergo elastic deformation, while other portions undergo plastic deformation. For example, in the embodiment of FIG. 11C, when leg 142 is pushed by the hammer against leg 140 conforming the legs to the curved surface of the anvil, leg 142 undergoes primarily plastic deformation, while leg 140 is primarily deformed elastically. The region around apex 144 undergoes heavily plastic deformation. Any elastically deformed portions of the clip will tend to recoil to their original, undeformed shapes after clip closure. This may reduce the tightness of clip closure, thereby reducing the security of the clip on the tissue between the clip legs.

To improve the tightness of closure, clip leg 142 is provided with one or more inverse arcuate portions 156, 158 which deform elastically rather than plastically when the clip is closed. In the embodiment of FIG. 12A, arcuate portion 156 will undergo primarily elastic deformation with the proximal portion 157 undergoing plastic deformation as the clip is closed. After closure, arcuate portion 156 will tend to recoil in a direction toward clip leg 140, thereby increasing the tightness of closure. In a second embodiment, shown in FIG. 12B, a second inverse arcuate portion 158 is provided in the proximal portion of leg 142. Both of inverse arcuate portions 156, 158 will undergo elastic deformation as the clip is closed, with the apex 144 and the bend 159 between the arcuate portions undergoing plastic deformation. After closure, any tendency of arcuate portions 156, 158 to recoil to their undeformed shapes will move the distal portion of leg 142 toward leg 140, again increasing the tightness of clip closure.

Usually, arcuate portions 156, 158 have radii R3, R4 approximately 10% larger than radius R1 of leg 140, which is typically in the range of 0.200 to 0.500 inches. The gap x between the distal tips of legs 140, 142 is preferably similar to that of the embodiment of FIG. 11C, e.g. in the range of 0.280-0.310 inches.

The preferred material for the clip is titanium, however, any non-toxic surgical metal may be used including stainless steel or tantalum.

In the method of the present invention, a clip applier as that illustrated in FIGS. 1-10 is provided, the clip applier having means for closing a clip, e.g. hammer 26 and anvil 16, the anvil 16 defining a slot open in the lateral direction, and means for advancing a clip to the closing means, e.g. belt 30 in barrel 10, shown in FIGS. 6 and 8. The clip applier is then positioned using handle 12 and/or rotating barrel 10 such that the slot in anvil 16 surrounds the tissue to which a clip is to be applied. A clip 14 is then advanced with its legs 15 pointing in the distal direction, as shown in FIGS. 2-4. The distal-most clip 24 is then rotated along track 28 in anvil 16 such that the tissue lies between the legs of the clip. Alternatively, the preceding three steps may be resequenced such that a clip is first advanced, then rotated, then positioned around the tissue when the clip is already in anvil 16. Finally, the clip is closed on the tissue.

In a further embodiment, the steps of rotating, closing and advancing clips are performed using a trigger, e.g. lever 18 on handle 12. Lever 18 is ratcheted in stages as described above, with a first stage corresponding to moving the lever to a partially depressed position toward handle 12 wherein a clip is rotated and positioned in anvil 16, a second stage corresponding to moving lever 18 to a fully-depressed position wherein a clip is closed by hammer 26, and a third stage corresponding to releasing lever 18 wherein clips are advanced on belt 30.

In another exemplary embodiment of the method of the present invention, the clip applier is repositioned, a second clip is advanced and rotated, and the clip is closed on the new site without removing the slot from the tissue. As described above, the clip applier advances clips facing distally then rotates the clips in anvil 16 to face in a lateral direction, thereby avoiding interference between the clip legs and any tissue positioned in the slot of anvil 16. This is a particular advantage of the present invention, allowing a surgeon to apply two or more clips along a section of tissue or duct by simply moving the slot in anvil 16 along the tissue or duct, without removing it therefrom.

The method of the present invention further provides for exerting tension on the tissue by pulling on the clip applier after the tissue has been positioned in the slot. This can be done for several purposes. First, the tissue can be pulled away from nearby tissue to avoid interfering with that tissue when the clip is closed. Known clip appliers suffer from the inability to exert tension on tissue, since the jaws are generally oriented distally, so that tissue cannot be pulled away from other tissue which might get in the way of the clip. Second, by applying such tension to the tissue, the tissue can be repositioned for better visibility. This is particularly advantageous during laparoscopic procedures, where the camera position is frequently somewhat limited, and the ability to pull the tissue in view of the camera to observe clip closure is highly desirable.

The clip applier of the present invention is especially well-adapted to such tensioning, since a clip can be rotated into the slot either before tissue has been pulled into tension, or after the user has pulled the tissue into a desired position and the tissue is being held in tension.

Using either technique, the clip can rotate into the slot without interfering with the tissue.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A surgical clip for use in a clip applier, the clip comprising:
    a first leg and a second leg connected at an apex and having distal ends separated by a gap so as to generally form a V-shape; and
    means disposed on a gripping surface of said first and second legs for gripping tissue, said means for gripping comprising at least a first recess having a pair of sidewalls extending from a floor of the recess to the gripping surface, at least one of said sidewalls being undercut such that a portion of the sidewall overlies the floor.

2. The surgical clip according to claim 1 wherein the recess comprises a longitudinal channel on each leg extending from a point near the apex to a point near the distal end.

3. The surgical clip according to claim 1 wherein the recess comprises a transverse groove, the means for gripping further comprising a plurality of such transverse grooves on the gripping surface.

4. The surgical clip according to claim 1 wherein the recess comprises a channel having a floor and an opening opposite the floor, the sidewalls extending from the floor to the opening and being inclined such that the floor is wider than the opening.

5. The surgical clip according to claim 4 wherein the floor is concave.

6. The surgical clip according to claim 1 wherein the recess comprises a pair of inclined channels intersecting at a point near the gripping surface, the recess sidewalls comprising sidewalls of the inclined channels.

7. The surgical clip according to claim 6 wherein the inclined channels intersect to form an opening at the gripping surface that is wider than each channel alone.

8. The surgical clip according to claim 7 wherein the recess has a triangular base disposed between the inclined channels, an apex of the triangular base being disposed below the opening.

9. The surgical clip according to claim 1 wherein the first leg has a first curvature and the second leg has a second curvature when the clip is open, said first and second curvatures selected such that the gripping surfaces of each leg are at least partially concave.

10. The surgical clip according to claim 1 wherein the clip is configured for closure with the first and second legs substantially parallel and in a third curvature, the first leg being longer than the second leg by a first distance selected such that the distal ends of the clip are even when the clip is closed.

11. The surgical clip according to claim 9 wherein at least one of the first and second legs has a distal portion having an inverse curvature such that the gripping surface on said distal portion is convex.

12. A surgical clip for use with a clip applier having a curved anvil for closing the clip in a curved shape, the clip comprising:
    a first leg and a second leg connected at an apex and having distal ends separated by a gap so as to generally form a V-shape, wherein the first leg is longer than the second leg by a first distance when the clip is in an open configuration.

13. The surgical clip according to claim 12 further comprising means disposed on a gripping surface of said first and second legs for gripping tissue, said means for gripping comprising at least a first recess on the gripping surface of each leg.

14. The surgical clip according to claim 13 wherein the recess has a pair of sidewalls extending from a floor of the recess to the gripping surface, at least a first of the sidewalls being undercut such that a portion of the sidewall overlies the floor.

15. The surgical clip according to claim 14 wherein the recess comprises a longitudinal channel extending from a point near the apex to a point near the distal end of each leg.

16. The surgical clip according to claim 14 further comprising a plurality of recesses on the gripping surface, the recesses comprising transverse grooves.

17. The surgical clip according to claim 12 wherein the first leg has a first curvature and the second leg has a second curvature when the clip is open, said first and second curvatures selected such that the gripping surfaces of each leg are at least partially concave.

18. The surgical clip according to claim 17 wherein at least one of the first and second legs has a distal portion having a curvature different than the curvature of a proximal portion of the leg.

19. The surgical clip according to claim 18 wherein the curvature of the distal portion is selected such that the gripping surface in the distal portion is convex.

20. The surgical clip according to claim 13 wherein a region of the gripping surface near the apex of the clip is substantially free of surface features.

21. The surgical clip according to claim 14 wherein the recess comprises a channel having a floor and an opening opposite the floor, the sidewalls extending from the floor to the opening and being inclined such that the floor is wider than the opening.

22. The surgical clip according to claim 21 wherein the floor is concave.

23. The surgical clip according to claim 14 wherein the recess comprises a pair of inclined channels intersecting at a point near the gripping surface, the recess sidewalls comprising sidewalls of the inclined channels.

24. The surgical clip according to claim 23 wherein the inclined channels intersect to form an opening at the gripping surface that is wider than each channel alone.

25. The surgical clip according to claim 24 wherein the recess has a triangular base disposed between the inclined channels, an apex of the triangular base being disposed below the opening.

26. The surgical clip according to claim 12 wherein the distal end of the second leg is beveled at an acute angle relative to an axis perpendicular to the gripping surface at the distal end.

27. A surgical clip for use with a clip applier having a curved anvil for closing the clip in a curved shape, the clip comprising:
    a first leg and a second leg connected at an apex and having distal ends separated by a gap so as to generally form a V-shape, wherein the first leg is longer than the second leg by a first distance when the clip is in an open configuration; and
    means disposed on a gripping surface of said first and second legs for gripping tissue, said means for gripping comprising a channel extending longitudinally on the gripping surface to a point near the distal end of each leg, the channel having a pair of sidewalls extending from a floor of the recess to the gripping surface, at least a first of the sidewalls being undercut such that a portion of the sidewall overlies the floor.

28. The surgical clip according to claim 27 wherein the means for gripping further comprises a plurality of transverse grooves on the gripping surface, the grooves intersecting the channel.

29. A surgical clip as in claim 28 wherein the transverse grooves are disposed at oblique angles on each side of the longitudinal channel.

30. A surgical clip as in claim 29 wherein the grooves from a V-pattern in the transverse plane with the V's opening toward the distal end of each leg.

31. A surgical clip as in claim 29 wherein the grooves form a V-pattern with the V's in each leg opening toward the apex.

32. A surgical clip as in claim 29 wherein the grooves form a V-pattern with the V's in one leg open toward the apex and the V's in the other leg open toward the distal end of the leg.

33. The surgical clip according to claim 27 wherein the first leg has a first curvature and the second leg has a second curvature when the clip is open, said first and second curvatures selected such that the gripping surfaces of each leg are at least partially concave.

34. The surgical clip according to claim 33 wherein at least one of the first and second legs has a distal portion having a curvature selected such that the gripping surface in the distal portion is convex.

35. The surgical clip according to claim 13 wherein the means for gripping comprises a plurality of slots drilled through the thickness of the clip.

36. The surgical clip according to claim 12 wherein the distal ends of the legs are substantially even in a closed configuration.

37. The surgical clip according to claim 27 wherein the distal ends of the legs are substantially even in a closed configuration.

38. A surgical clip for use in a clip applier, the clip comprising:
a first leg and a second leg connected at an apex and having distal ends separated by a gap so as to generally form a V-shape;
means disposed on a gripping surface of said first and second legs for gripping tissue, said means for gripping comprising at least a first recess having a pair of sidewalls extending from a floor with an opening opposite the floor, at least a first of the sidewalls being undercut such that the distance between the sidewalls at the floor is greater than the distance between the sidewalls at the opening.

39. The surgical clip according to claim 38 wherein the recess comprises a longitudinal channel on each leg extending from a point near the apex to a point near the distal end.

40. The surgical clip according to claim 38 wherein the recess comprises a transverse groove, the means for gripping further comprising a plurality of such transverse grooves on the gripping surface.

41. The surgical clip according to claim 38 wherein the first leg has a first curvature and the second leg has a second curvature when the clip is open, said first and second curvatures selected such that the gripping surfaces of each leg are at least partially concave.

42. The surgical clip according to claim 38 wherein the clip is configured for closure with the first and second legs substantially parallel and in a third curvature, the first leg being longer than the second leg by a first distance selected such that the distal ends of the clip are even when the clip is closed.

43. The surgical clip according to claim 41 wherein at least one of the first and second legs has a distal portion having an inverse curvature such that the gripping surface on said distal portion convex.

44. A surgical clip for use with a clip applier having a curved anvil for closing the clip in a curved shape, the clip comprising:
a first leg and a second leg connected at an apex and having distal ends separated by a gap so as to generally form a V-shape, wherein the first leg is longer than the second leg by a first distance selected such that the distal ends of the clip are even when the clip is closed with the legs substantially parallel in the curved shape.

45. The surgical clip according to claim 44 further comprising means disposed on a gripping surface of said first and second legs for gripping tissue, said means for gripping comprising at least a first recess on the gripping surface of each leg.

46. The surgical clip according to claim 45 wherein the recess has a pair of sidewalls extending from a floor with an opening opposite the floor, at least a first of the sidewalls being undercut such that the distance between the sidewalls at the floor is greater than the distance between the sidewalls at the opening.

47. The surgical clip according to claim 46 wherein the recess comprises a longitudinal channel extending from a point near the apex to a point near the distal end of each leg.

48. The surgical clip according to claim 46 further comprising a plurality of recesses on the gripping surface, the recesses comprising a plurality of transverse grooves on the gripping surface.

49. The surgical clip according to claim 44 wherein the first leg has a first curvature and the second leg has a second curvature when the clip is open, said first and second curvatures selected such that the gripping surfaces of each leg are at least partially concave.

50. The surgical clip according to claim 49 wherein at least one of the first and second legs has a distal portion having a curvature different than the curvature of a proximal portion of the leg.

51. The surgical clip according to claim 50 wherein the curvature of the distal portion is selected such that the gripping surface in the distal portion is convex.

52. The surgical clip according to claim 45 wherein a region of the gripping surface near the apex of the clip is substantially free of surface features.

53. The surgical clip according to claim 45 wherein the recess has a pair of sidewalls extending from a floor with an opening opposite the floor, the sidewalls being inclined such that the channel is wider at the opening than at the floor.

54. The surgical clip according to claim 46 wherein the floor is concave.

55. The surgical clip according to claim 44 wherein the distal end of the second leg is beveled at an acute angle relative to an axis perpendicular to the gripping surface at the distal end.

56. A surgical clip for use with a clip applier having a curved anvil for closing the clip in a curved shape, the clip comprising:
a first leg and a second leg connected at an apex and having distal ends separated by a gap so as to generally form a V-shape, wherein the first leg is longer than the second leg by a first distance selected such that the distal ends of the clip are even when the clip is closed with the legs substantially parallel in the curved shape; and means disposed on a gripping surface of said first and second legs for gripping tissue, said means for gripping comprising a channel extending longitudinally on the gripping surface to a point near the distal end of each leg, the channel having a pair of sidewalls extending from a floor with an opening opposite the floor, at least a first of the sidewalls being undercut such that the distance between the sidewalls at the floor is greater than the distance between the sidewalls at the opening.

57. The surgical clip according to claim 56 wherein the means for gripping further comprises a plurality of transverse grooves on the gripping surface, the grooves intersecting the channel.

58. A surgical clip as in claim 57 wherein the transverse grooves are disposed at oblique angles on each side of the longitudinal channel.

59. A surgical clip as in claim 58 wherein the grooves from a V-pattern in the transverse plane with the V's opening toward the distal end of each leg.

60. A surgical clip as in claim 58 wherein the grooves form a V-pattern with the V's in each leg opening toward the apex.

61. A surgical clip as in claim 58 wherein the grooves form a V-pattern with the V's in one leg open toward the apex and the V's in the other leg open toward the distal end of the leg.

62. The surgical clip according to claim 56 wherein the first leg has a first curvature and the second leg has a second curvature when the clip is open, said first and second curvatures selected such that the gripping surfaces of each leg are at least partially concave.

63. The surgical clip according to claim 62 wherein at least one of the first and second legs has a distal portion having a curvature selected such that the gripping surface in the distal portion is convex.

64. The surgical clip according to claim 56 wherein the means for gripping further comprises a plurality of slots drilled through the thickness of the clip.

* * * * *

UNITED STATES PATENT AND TRADEMARK OFFICE
CERTIFICATE OF CORRECTION

PATENT NO. : 5,269,792
DATED : December 14, 1993
INVENTOR(S) : Kovac, et. al.

It is certified that error appears in the above-indentified patent and that said Letters Patent is hereby corrected as shown below:

On the Title page, item [75], inventors: should be as follows:

Inventors: Terrance Kloeckl, Palo Alto; Tim Kovac, Los Gatos; Jay Daulton, San Jose, all of Calif.; Peter F. Costa, Winthrop; William A. Holmes, Marblehead, both of Mass.; Richard J. Saunders, Redwood City, Calif.

Signed and Sealed this

Seventh Day of June, 1994

Attest:

BRUCE LEHMAN

*Attesting Officer*     *Commissioner of Patents and Trademarks*